United States Patent [19]

Brenholdt

[11] Patent Number: 4,648,712

[45] Date of Patent: Mar. 10, 1987

[54] APPARATUS AND METHOD FOR ANALYZING PARAMETERS OF A FIBROUS SUBSTRATE

[75] Inventor: Irving R. Brenholdt, Stratford, Conn.

[73] Assignee: Champion International Corporation, Stamford, Conn.

[21] Appl. No.: 698,226

[22] Filed: Feb. 4, 1985

[51] Int. Cl.$^4$ .................................... G01N 21/86
[52] U.S. Cl. ................................. 356/73; 162/49; 162/263; 250/559; 250/571; 356/429; 356/432
[58] Field of Search ............ 356/73, 238, 429, 430, 356/431, 432, 435; 250/559, 562, 563, 571, 572; 162/49, 263

[56] References Cited

U.S. PATENT DOCUMENTS 3,193,688 7/1965 Morton et al. ............... 356/238 X
3,207,901 9/1965 Barker, Jr. ..................... 250/559
3,437,823 4/1969 Joyce ......................... 162/263 X Primary Examiner—Vincent P. McGraw
Attorney, Agent, or Firm—Evelyn M. Sommer

[57] ABSTRACT

A radiation sensor provides on-line measurement of web MD/CD fiber orientation ratio, formation indexes of multiple spatial frequencies, and optical density as it relates to basis weight. A light source illuminates one side of a substrate to be measured. The radiation passing through the substrate is detected by a pair of detectors having fields of view along narrow strips which are perpendicular to each other. The combined field of view is scanned in a repetitive pattern traversing an area on the substrate to be analyzed. The detector outputs are processed to provide fiber orientation ratio, formation, and basis weight measurements.

22 Claims, 6 Drawing Figures

APPARATUS AND METHOD FOR ANALYZING PARAMETERS OF A FIBROUS SUBSTRATE

BACKGROUND OF THE INVENTION

This invention relates to an apparatus and method for analyzing parameters of a fibrous substrate such as paper, and more particularly to evaluating the fiber orientation ratio, formation, and basis weight of paper.

In the papermaking art, the term "fiber orientation" is used to describe the general arrangement of fibers within a paper substrate. Paper fibers are not usually uniformly arranged in all directions in the plane of the paper. Instead, a proportion of fibers will be aligned in the "machine direction" ("MD") of the paper and others will be oriented perpendicular thereto, in the "cross direction" ("CD") of the paper. Other fibers will be oriented randomly between the machine direction and cross direction. Fibers in the machine direction will be those which are longitudinally aligned in the direction in which the paper traveled as a web in the paper manufacturing machinery. The cross direction is perpendicular to the direction of web travel through the paper making machinery.

Fiber orientation is a key factor in the strength and anisotropy of paper. Factors which influence fiber orientation include the design of the head box which holds the paper pulp, the paper pulp, the differential velocity between the pulp jet and the endless wire conveyor which transports the pulp in mat form, and the rate of dewatering used in the paper manufacturing process.

It has been demonstrated by various investigators that orientation of the fibrous material comprising a web has a distinct relationship to certain important physical properties of the web. Some of these properties are commonly known as tensile strength, Young's modulus, shear modulus, tension at rupture, normal strain, shear strain, bursting strength, etc.

For some products a random fiber orientation in large and small areas alike is desirable. In other products it is desirable to obtain a high ratio of fiber orientation in one direction as opposed to all other directions. Such a product would tear readily in a direction parallel to the highly oriented direction and provide maximum strength normal to the parallel direction.

Fiber orientation during web manufacture is controlled by adjusting the velocity of the pulp furnish jet relative to the velocity of the web forming wire. Orientation randomness is maximized by matching the two velocities exactly. Orientation in the machine direction is maximized by precisely controlling the wire and jet at slightly different velocities.

Several methods for determining the fiber orientation are known in the prior art. These include various kinds of tensile strength tests, in which the tensile strength in different directions of the paper are measured. Usable results are only obtained by these methods if a high correlation exists between tensile strength and orientation, which is not always the case. Another method for determining fiber orientation is the so called "staining" method. Stained fibers are added to the pulp and the fibers lying in different directions are individually counted. This technique is tedious, and is not suitable for use during the production of commercial products.

Various methods for the determination of fiber orientation based on the defraction of radiation are also known. For example, x-ray and neutron defraction methods have been studied, but their ultimate usefulness has not been determined. A difficulty present with such methods is that of interpreting the defraction patterns obtained. Ultrasonic techniques have also been employed to analyze fiber orientation, which utilize the production of waves in the paper.

In U.S. Pat. No. 3,807,868, a method is disclosed for determining the fiber orientation in paper by using reflected light. A polarized light beam, such as a laser beam, is directed at right angles against the plane of the paper. The intensity of the light reflected by the paper under a given angle is observed in two planes at right angles to each other. Two quantities are formed from the intensity of the reflected light. One results by conducting the reflected light to pass through a polarizer having a polarizing plane parallel to the plane of polarization of the light beam. The other quantity is obtained by conducting the reflected light to pass through a polarizer with its polarizing plane perpendicular to the plane of polarization of the light beam. The differences of the two quantities observed in both planes are calculated, and the ratio of these differences is used as a measure of the fiber orientation. The method disclosed in the '868 patent utilizes a stationary light source and detector arrangement.

Another parameter of interest in fibrous substrates such as paper is known as "formation". When a sheet of paper looks uniform on viewing it up to the light, its formation is called good, while an irregular, grainy or blotchy structure may be described as such or may be called "wild" formation. U.S. Pat. Nos. 3,435,240; 3,435,242; and 3,563,667 each disclose apparatus for measuring the formation of paper. In the '240 and '242 patents, two photomultipliers are directed toward respective large and small areas on a moving web of paper. The fields of view of the photomultipliers overlap such that the larger surrounds the smaller. The transmittance from a small spot of light on the paper is compared with that of a much larger area of light thereon, to provide a signal representing formation. In the '667 patent, a formation measurement is made by passing a light beam through the paper and letting it act on a light sensitive element on the other side thereof. A current is produced which is proportional to the light intensity and is composed of direct current and alternating current components. The alternating current component represents the non-uniformity in paper formation.

Another characteristic of paper which is of importance is its basis weight. The basis weight of paper, expressed in pounds, is the weight of a ream of 500 sheets of size 24" by 36". Because of inherent imperfections in the manufacturing process, the paper industry has for years been plagued by variations in basis weight across the sheet during manufacture. Various apparatus for measuring the basis weight of paper are disclosed in U.S. Pat. Nos. 3,207,901; 3,687,802; and 4,098,641. The '802 patent determines basis weight by using a gamma or beta ray gauge. The '901 and '641 patents both determine basis weight by passing light through a moving web of paper. The amount of light transmitted through the paper substrate is a function of the paper's basis weight.

It would be advantageous to provide a method and apparatus for determining various parameters of a fibrous substrate, such as fiber orientation, formation, and basis weight. Such apparatus and method should be highly accurate to provide meaningful results either on line in a manufacturing process or as part of a quality control procedure for a manufactured substrate. Equipment having this capability would provide immediate quantitative feedback to the web maker. Such feedback could ultimately provide a closed loop to insure the constant jet to wire velocity ratio so important to the manufacturer. The present invention relates to such a method and apparatus.

SUMMARY OF THE INVENTION

In accordance with the present invention, apparatus is provided for analyzing a fibrous substrate such as paper to evaluate its fiber orientation ratio, formation index, and basis weight. The apparatus includes a light source for illuminating one side of a substrate to be analyzed. First and second light detectors detect light from the light source which has passed through to the other side of the substrate. The light detectors produce outputs proportional to the light detected thereby. Means are provided for limiting the field of view of the first light detector to a narrow strip along a first direction, e.g., the machine direction of a paper substrate. Means are provided for limiting the field of view of the second light detector to a narrow strip along a second direction, e.g., the cross direction of a sheet of paper. Means are also provided for jointly scanning the fields of view of the light detectors in a repetitive pattern traversing the first and second directions to cover an area on the substrate being analyzed. Appropriate filters eliminate components in the outputs of the first and second detectors below a predetermined frequency. Means are provided for processing the filtered outputs of the detectors to produce a combined signal indicative of the ratio of fibers of the substrate oriented in the first direction to those oriented in the second direction.

Typically, the fields of view of the first light detector (first direction) and second light detector (second direction) are perpendicular to each other. Further, the narrow strips which limit the detectors' fields of view can be optically superimposed to form a cross for scanning the substrate. The repetitive pattern in which the cross is scanned can, for example, be a circle or a rosette. Such scanning can be accomplished using a rotating wedge prism for the circular pattern and a pair of counterrotating wedge prisms for the rosette pattern.

By summing the outputs of the first and second light detector means, and filtering the summed outputs to resolve first and second spacial frequencies, signals indicative of the formation structure of the substrate can be produced and, if desired, displayed.

The apparatus can also sum the outputs of the first and second detectors, compare the magnitude thereof to a reference magnitude to compute a difference signal, and adjust the brightness of the light source in accordance with the difference signal to maintain the amount of light passing through the substrate at a constant level, and thereby produce a signal indicative of the basis weight of the substrate.

In accordance with the method of the present invention, fiber orientation ratio is analyzed in a fibrous substrate by first directing light from a light source through a substrate to be analyzed. Light passing through the substrate is then viewed with a first detector having a field of view limited to a slit in a first direction and a second detector having a field of view limited to a slit in a second direction perpendicular to the first direction. The fields of view of the first and second detectors are scanned in a repetitive pattern traversing the first and second directions to cover an area on the substrate being analyzed. The outputs of the first and second detectors are processed, during the scanning step, to produce a signal indicative of the ratio of fibers of the substrate oriented in the direction of the first slit to those oriented in the direction of the second slit. The formation index and basis weight of the substrate are determined by further processing the outputs of the first and second detectors.

DETAILED DESCRIPTION OF THE INVENTION

Figure 1:
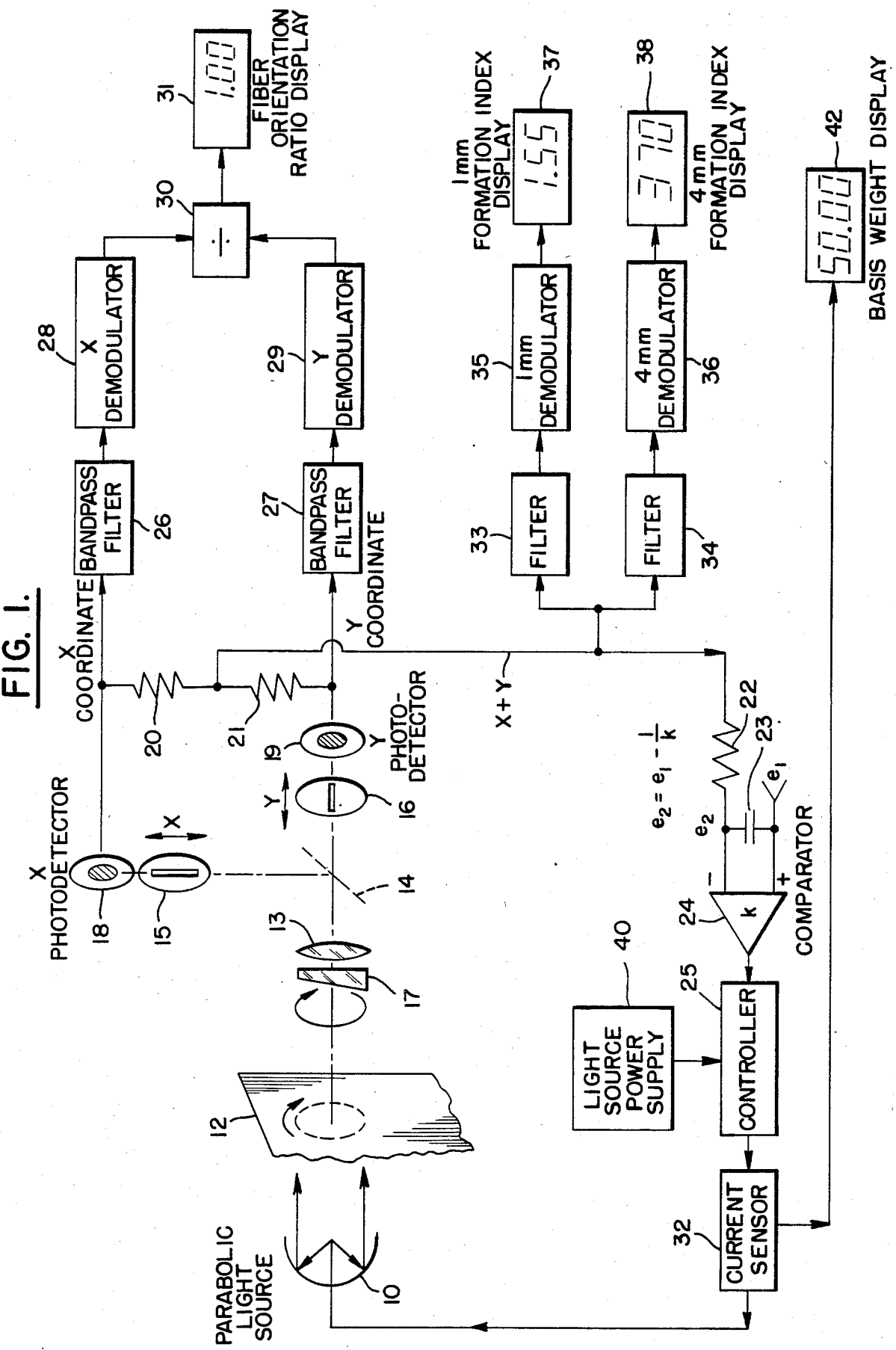
FIG. 1 is a schematic block diagram of the apparatus of the present invention.

Referring to FIG. 1, a light source 10 illuminates a test sample or web 12 from a preferred backside or underside such that light is transmitted through the web. Light source 10 can comprise, for example, a parabolic lamp of a type well known in the art. The word "light" is used in its broadest sense throughout this specification and claims, and those skilled in the art will appreciate that other radiation sources, such as an infrared only source, are encompassed thereby. The present claims are intended to cover all such radiation sources, whether or not in the visible light spectrum.

An objective lens 13 forms an image of the web 12 including fibers and fiber flocs. The image is transmitted through a 50/50 beam splitter 14 to two focal planes x and y in which are vertical and horizontal slits 15 and 16, respectively. The slits 15 and 16 are identical and have aspect ratios of approximately 250 to 1 where the small dimension is equivalent to a minimum fiber diameter of 0.025 mm. A wedge prism 17 deflects the image of the web 12 through an angle, for example 6 degrees. The wedge prism 17 is rotated at a constant speed, for example 900 rpm, by a motor (not shown).

Radiant optical energy in the x and y images enters the slits 15 and 16 and is collected by x and y photodetectors 18 and 19, where it is converted to x and y coordinate voltages, respectively.

The x and y coordinate voltages are summed through the equal resistances 20 and 21. The sum $x+y$ is integrated by the action of the combination of resistor 22 and the capacitor 23. The bandpass characteristics of the resistance/capacitance combination could be, for example, from 0 to 100 HZ.

The integrated sum of x and y, designated "$e_2$", is inverted by the comparator 24. The inverted sum is compared to a reference voltage "$e_1$", which functions as a calibration and control voltage. The comparator 24 amplifies its input signal by a constant "k". The output is fed to a light source power controller 25, thus completing a negative feedback control loop. Controller 25 adjusts the amount of power from a power supply 40, which supplies power to drive light source 10.

As the optical density of the web 12 is increased, the intensity of light source 10 is increased in direct proportion through the action of the feedback control loop.

Thus, the system sensitivity to individual fibers and groups of fibers ("flocs") is maintained.

The rotation of the wedge prism 17 induces an angular velocity in the optical image. As the image moves past the slits 15 and 16, electrical impulses are generated by the passage of fibers and flocs of different sizes. For example, at a scan angle of 6 degrees and a rotational rate of 900 rpm, the impulses due to fibers and flocs of up to ten fibers each would correspond to temporal frequencies of 10 kHz to 100 kHz and spatial frequencies of 200 microns and 20 microns, respectively.

The image of a fiber or group of fibers passing the slits 15, 16 and oriented parallel to the slits produces the maximum change in optical contrast and hence the largest output voltage in the band of frequencies referred to above. Conversely, the image of a fiber or group of fibers passing the slits 15, 16 and oriented normal to the slits produces the minimum change in optical contrast and hence the smallest output voltage in the band of frequencies referred to above. Voltages from photodetectors 18 and 19, after passing through bandpass filters 26 and 27, are demodulated by the demodulators 28 and 29, providing x and y dc voltages proportional to the number of fibers oriented in each of the two directions, respectively. The two voltages are fed to an electronic divider circuit 30 and the ratio is displayed on a conventional display 31. Display 31 can comprise, for example, any digital display well known in the art.

When the web analyzer system is properly calibrated by adjusting the reference voltage $e_1$ which is input to comparator 24, then for a given type of web, for example, kraft paper, the current to the light source, and hence the light source energy, is proportional to "basis weight". A current sensor 32 coupled between controller 25 and light source 10 provides an output proportional to the intensity of light source 10. This output can be displayed on a conventional display 42 as an indication of the basis weight of the web.

In addition, certain components of the sum of the outputs of photodetectors 18 and 19 can be removed, for example, by filters 33 and 34. These components are sometimes used to characterize web "formation". Filter 33 passes the temporal frequency 2000 Hz, which in this system corresponds to a spatial frequency of 1 mm. The filter 34 passes the temporal frequency 500 Hz, which in this system corresponds to a spatial frequency of 4 mm. These components are demodulated by demodulators 35 and 36 and displayed, on displays 37 and 38, as 1 mm and 4 mm formation indexes, respectively.

Figure 2:
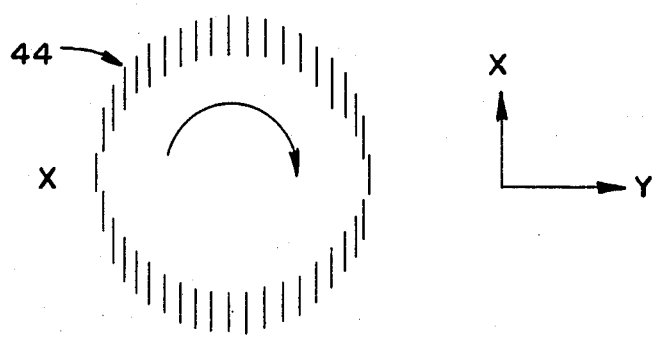
FIGS. 2 and 3 are diagrams illustrating the concept of coaxial nutation.
Figure 3:
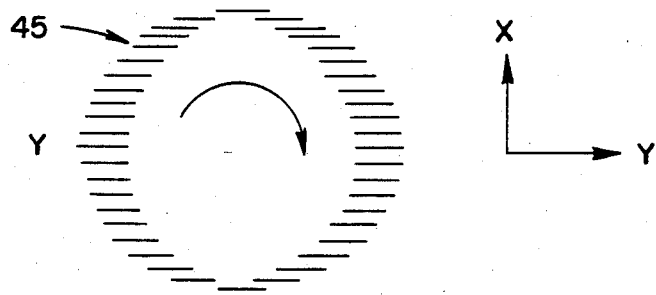

In the scanning means described, the optical image is scanned or "nutated" in a circle and the slits 18 and 19 are stationary. For the purpose of clarity, the two slits 15 and 16, which are normal to each other, can be imagined as nutating about a common axis penetrating the web. The concept of coaxial nutation is illustrated in FIGS. 2 and 3. FIG. 2 shows the x component of the image, and FIG. 3 shows the y component. The images shown in FIGS. 2 and 3 are superimposed, during operation of the present apparatus, by 50/50 beam splitter 14.

Figure 4:
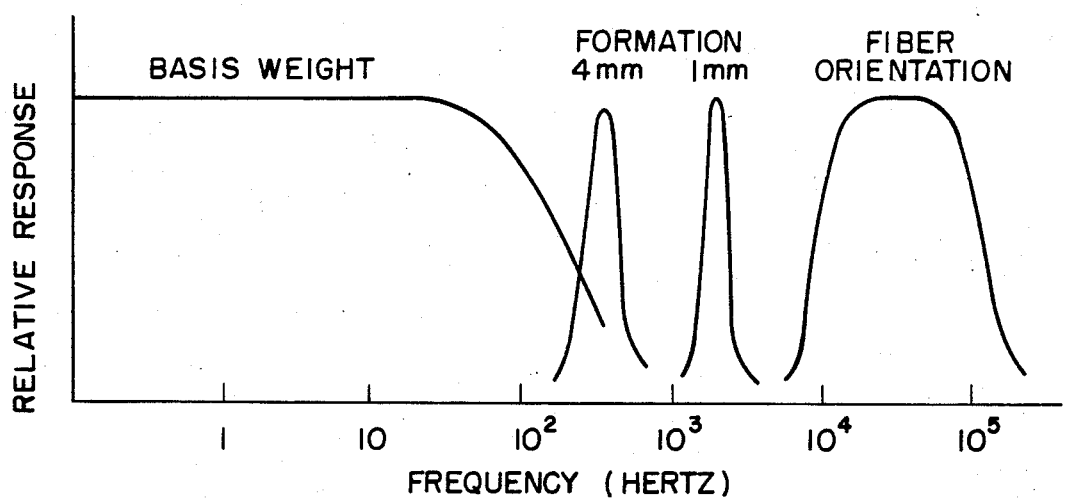
FIG. 4 is a graph illustrating the frequency spectrum of information utilized in a paper web analyzer system constructed in accordance with the present invention.

FIG. 4 shows the frequency spectrum of information utilized in the web analyzer system. "Basis weight" extends from zero to, for example, 100 Hz. 4 mm "formation" peaks at, for example, 500 Hz. 1 mm "formation" peaks at, for example, 2000 Hz. "Fiber orientation" includes a band from 10 kHz to 100 kHz.

Figure 5:
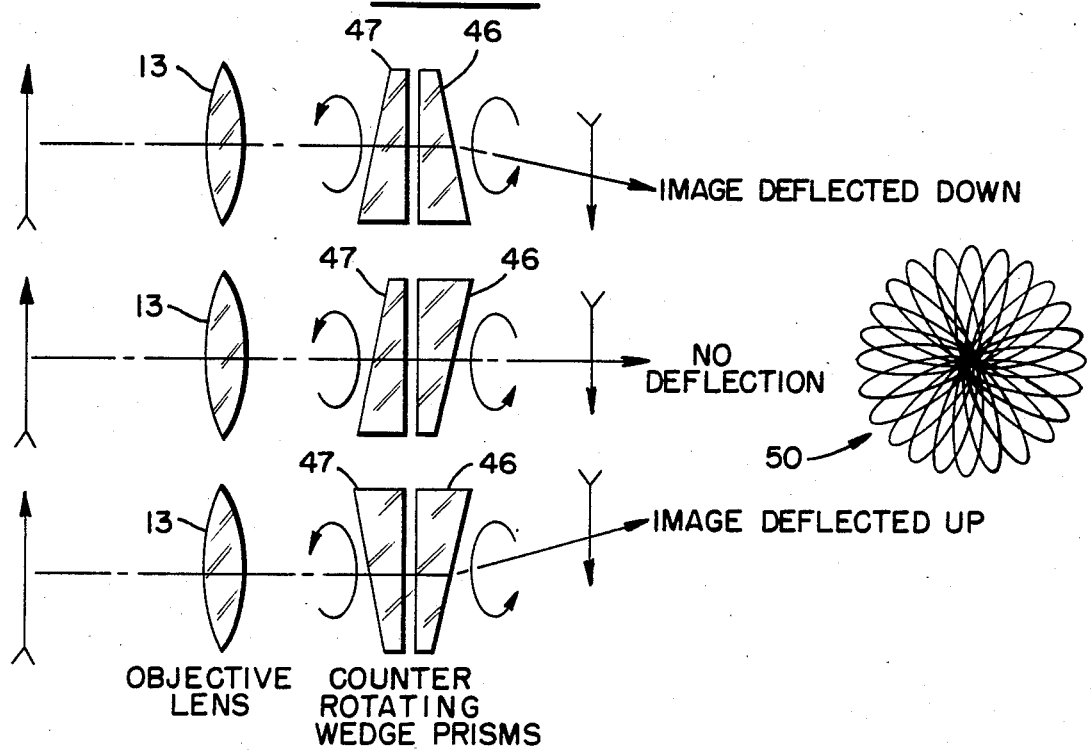
FIG. 5 is a diagram illustrating the use of counter rotating wedge prisms to scan a rosette pattern.
Figure 6:
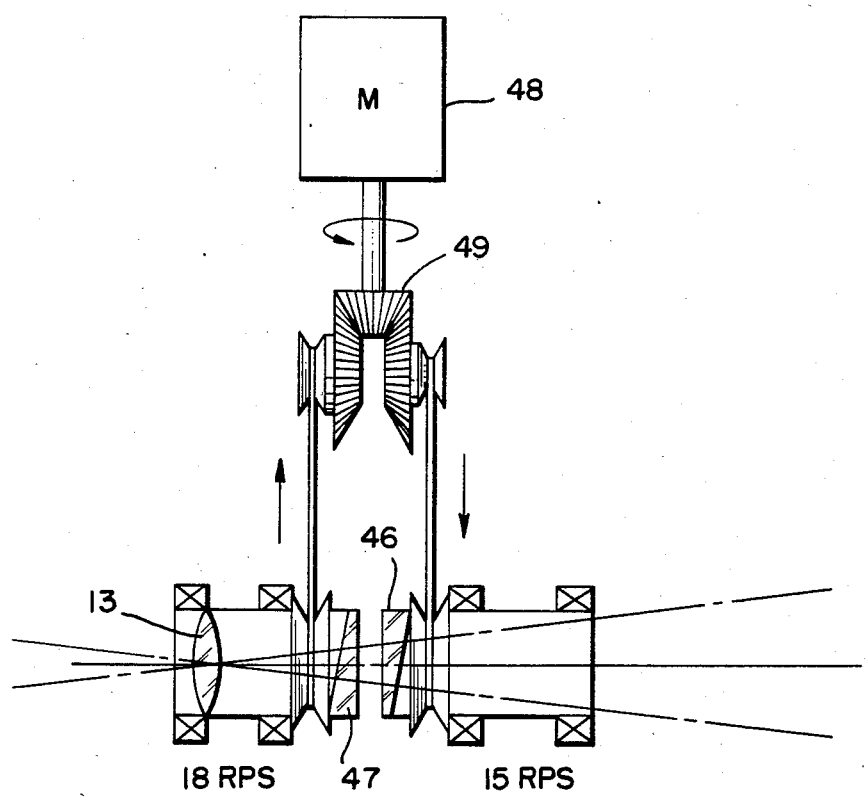
FIG. 6 is a diagram illustrating a mechanical arragement for rotating the prisms shown in FIG. 5.

A second scanning method is illustrated in FIG. 5. This method is preferred since it scans 100% of a disc-like area in a rosette pattern, as compared to the first method, which scans only the periphery of a circle. Instead of a single rotating wedge prism 17 as shown in FIG. 1, two counter-rotating wedge prisms 46, 47 are used. The prisms 46, 47 rotate at different rates of speed to produce a rosette pattern 50. In the three different orientations shown in FIG. 5, the image is either deflected down, deflected up, or undergoes no deflection through the action of the counter-rotating wedge prisms 46, 47. The result is the rosette pattern 50 shown. Mechanical configuration of the scanner is shown in FIG. 6.

The two wedge prisms 46, 47 are rotated in opposite directions at slightly different rates by a motor 48 and gear train 49, producing a complete rosette scan pattern. The example given shows one prism rotated at 15 revolutions per second and a second at 18 revolutions per second. A scan would be completed in 3 seconds (18 minus 15).

I claim:

1. Apparatus for analyzing a fibrous substrate such as paper to evaluate the orientations of fibers therein comprising:
   light source means for illuminating one side of a substrate to be analyzed;
   first and second light detector means for detecting light from said light source which has passed through to the other side of the substrate and producing an output proportional to the light detected thereby;
   means for limiting the field of view of said first light detector means to an elongated narrow strip along a first direction;
   means for limiting the field of view of said second light detector means to an elongated narrow strip along a second direction;
   means for jointly scanning the fields of view of said light detectors in a repetitive pattern traversing said first and second directions to cover an area on the substrate being analyzed;
   means for filtering the output of said first detector to eliminate components thereof below a predetermined frequency;
   means for filtering the output of said second detector to eliminate components thereof below a predetermined frequency; and
   means for processing the filtered outputs of said detectors to produce a combined signal indicative of the ratio of fibers of said substrate oriented in said first direction to those oriented in said second direction.

2. The apparatus of claim 1 wherein said first direction is perpendicular to said second direction.

3. The apparatus of claim 2 wherein said narrow strips are optically superimposed to form a cross for scanning in said repetitive pattern.

4. The apparatus of claim 3 wherein the repetitive pattern in which said cross is scanned is a circle.

5. The apparatus of claim 3 wherein the repetitive pattern in which said cross is scanned is a rosette.

6. The apparatus of claim 4 wherein said means for scanning comprises a rotating wedge prism disposed between said substrate and detector means.

7. The apparatus of claim 5 wherein said means for scanning comprises a pair of counter-rotating wedge prisms disposed between said substrate and detector means, and means for rotating the prisms in said pair at different rates of speed.

8. The apparatus of claim 1 further comprising:
means for summing the outputs of said first and second light detector means;
means for filtering the summed outputs to resolve first and second spatial frequencies; and
means for processing said first and second spatial frequencies to produce signals indicative of the formation structure of said substrate.

9. The apparatus of claim 1 further comprising:
means for summing the outputs of said first and second light detector means;
means for comparing the magnitude of the summed outputs to a reference magnitude and computing a difference signal therefrom; and
means for adjusting the brightness of said light source in accordance with said difference signal to maintain the amount of light passing through said substrate at a constant level, thereby producing a signal indicative of the basis weight of said substrate.

10. The apparatus of claim 1 wherein said substrate is a web of paper moving through a paper manufacturing machine.

11. Apparatus for analyzing properties of a fibrous substrate comprising:
means for directing light from a light source through a substrate to be analyzed;
a first light detector;
first slit means for limiting the field of view of said first light detector to an elongated narrow strip in a first direction;
a second light detector;
second slit means for limiting the field of view of said second light detector to an elongated narrow strip in a second direction generally perpendicular to said first direction;
optical means for superimposing and scanning the limited fields of view of said detectors across said substrate in said first and second directions to monitor light passed through the substrate from said source and produce output signals in accordance therewith; and
means for processing the output signals from said detectors to provide information as to specific properties of said substrate.

12. The apparatus of claim 11 wherein said processing means includes:
bandpass filter and demodulator means coupled to said first and second detectors for passing and demodulating output signals from said detectors having frequencies within a predetermined range indicative of fibers in said substrate; and
means for providing a combined signal from said filtered, demodulated signals indicative of the ratio of fibers in said substrate oriented in said first direction to those oriented in said second direction.

13. The apparatus of claim 12 wherein said processing means includes:
means for summing the outputs of said first and second detectors;
means for filtering the summed outputs to resolve first and second spatial frequencies; and
means for processing said first and second spatial frequencies to produce signals indicative of the formation structure of said substrate.

14. The apparatus of claim 13 wherein said filtering means resolves spatial frequencies of about 1 millimeter and about 4 millimeters.

15. The apparatus of claim 13 further comprising:
means for comparing the magnitude of the summed outputs to a reference magnitude and computing a difference signal therefrom; and
means for adjusting the brightness of said light source in accordance with said difference signal to maintain the amount of light passing through the substrate at a constant level, thereby producing a signal indicative of the basis weight of said substrate.

16. The apparatus of claim 11 wherein said optical means comprises:
a beam splitter for directing light incident thereon to said first and second light detectors; and
a rotating wedge prism disposed between said substrate and said beam splitter.

17. The apparatus of claim 16 further comprising a counter-rotating wedge prism in series with and rotating at a different rate of speed than said rotating wedge prism.

18. The apparatus of claim 11 wherein said superimposed limited fields of view form a cross.

19. A method for analyzing the fiber orientation ratio of a fibrous substrate such as paper comprising the steps of:
directing light from a light source through a substrate to be analyzed;
viewing the light passing through the substrate with a first detector having a field of view limited to an elongated slit in a first direction and a second detector having a field of view limited to an elongated slit in a second direction perpendicular to said first direction;
scanning the fields of view of said first and second detectors in a repetitive pattern traversing said first and second directions to cover an area on the substrate being analyzed; and
processing the outputs of said first and second detectors during said scanning step to produce a signal indicative of the ratio of fibers of said substrate oriented in the direction of said first slit to those oriented in the direction of said second slit.

20. The method of claim 19 comprising the further steps of:
summing the outputs of said first and second detectors during said scanning step to produce a combined sensor signal; and
filtering said combined sensor signal to resolve a first spatial frequency indicative of the formation index of said substrate at the first spatial frequency.

21. The method of claim 20 comprising the further step of:
filtering said combined sensor signal to resolve a second spatial frequency indicative of the formation index of said substrate at the second spatial frequency.

22. The method of claim 21 comprising the further steps of:
comparing the magnitude of the combined sensor signal to a reference magnitude and computing a difference signal therefrom;
adjusting the brightness of said light source by varying the magnitude of current applied thereto in accordance with said difference signal to maintain the amount of light passing through the substrate at a constant value; and
determining the basis weight of said substrate from the magnitude of the current applied to said light source.

* * * * *